US008236858B2

(12) United States Patent
Peleg-Shulman et al.

(10) Patent No.: US 8,236,858 B2
(45) Date of Patent: Aug. 7, 2012

(54) SUBSTITUTED ARYL-INDOLE COMPOUNDS AND THEIR KYNURENINE/KYNURAMINE-LIKE METABOLITES AS THERAPEUTIC AGENTS

(75) Inventors: Tal Peleg-Shulman, Tel Aviv (IL); Moshe Laudon, Kfar Saba (IL); Dvorah Daily, Herzliya (IL)

(73) Assignee: Neurim Pharmaceuticals (1991) Ltd., Tel Aviv (IL)

( * ) Notice: Subject to any disclaimer, the term of this patent is extended or adjusted under 35 U.S.C. 154(b) by 0 days.

(21) Appl. No.: 13/197,462

(22) Filed: Aug. 3, 2011

(65) Prior Publication Data
US 2011/0319494 A1    Dec. 29, 2011

Related U.S. Application Data

(60) Continuation of application No. 12/611,373, filed on Nov. 3, 2009, now Pat. No. 8,003,702, which is a division of application No. 11/865,437, filed on Oct. 1, 2007, now Pat. No. 7,622,495.

(60) Provisional application No. 60/848,642, filed on Oct. 3, 2006.

(51) Int. Cl.
*A61K 31/136* (2006.01)
*A61K 31/137* (2006.01)
(52) U.S. Cl. .................... 514/646; 514/649
(58) Field of Classification Search ............ 514/646; 564/440
See application file for complete search history.

(56) References Cited

U.S. PATENT DOCUMENTS
2,870,162 A    1/1959    Speeter et al.

FOREIGN PATENT DOCUMENTS
| GB | 2192001 A | 12/1987 |
| JP | 49-101348 A | 9/1974 |
| JP | 20007626 A | 1/2000 |
| WO | 0059504 A1 | 10/2000 |
| WO | 0228347 A2 | 4/2002 |
| WO | 2004112690 A2 | 12/2004 |
| WO | 2006032631 A1 | 3/2006 |

OTHER PUBLICATIONS

Database Beilstein [Online] Beilstein Institute for Organic Chemistry, Frankfurt-Main, DE; Database accession No. 149035 (BRN) abstract (Plieninger: Chem. Ber., 87: 127 (1954)).
Database Beilstein [Online] Beilstein Institute for Organic Chemistry, Frankfurt-Main, DE; Database accession No. 231117 (BRN) abstract (Walker, J. Am. Chem. Soc., 77:3844-3848 (1955)).
Database Beilstein [Online] Beilstein Institute for Organic Chemistry, Frankfurt-Main, DE; Database accession No. 482205 (BRN) abstract (Biswas, Jackson: Tetrahedron, 25: 227 (1969)).
Database Beilstein [Online] Beilstein Institute for Organic Chemistry, Frankfurt-Main, DE; Database accession No. 4869227 (BRN) abstract (Macor et al., Heterocycles, 35(1): 349-365 (1993)).
Database Beilstein [Online] Beilstein Institute for Organic Chemistry, Frankfurt-Main, DE; Database accession No. 7434680 (BRN) abstract (Koshima, et al., J. Org. Chem., 61(7): 2352-2357 (1996)).
Database Beilstein [Online] Beilstein Institute for Organic Chemistry, Frankfurt-Main, DE; Database accession No. 9920998 (BRN) abstract (Pchalek et al., Tetrahedron, 61(1): 77-82 (2005)).
Database Beilstein [Online] Beilstein Institute for Organic Chemistry, Frankfurt-Main, DE; Database accession No. 173665, 200892, 206864, 216406 (BRNs) abstract (Qureshi et al., Pakistan J. Scient. Ind. Res., 1: 101 (1958)).
Database Beilstein [Online] Beilstein Institute for Organic Chemistry, Frankfurt-Main, DE; Database accession No. 238134 (BRN) abstract (Gaedcke et al., Arch. Pharm., 313(2): 166-173 (1980)).
Database Beilstein [Online] Beilstein Institute for Organic Chemistry, Frankfurt-Main, DE; Database accession No. 9563276, 9567260 (BRNs) abstract (Yadav et al., Tetrahedron Lett., 44(45): 8331-8334 (2003)).
Database Beilstein [Online] Beilstein Institute for Organic Chemistry, Frankfurt-Main, DE; Database accession No. 648738 (BRN) abstract (Stetter et al., Chem. Ber., 110: 1971-1977 (1977)).
Database Beilstein [Online] Beilstein Institute for Organic Chemistry, Frankfurt-Main, DE; Database accession Nos. 4513710, 4523075, 4533680, 4533997, 4543629 (BRNs) abstract (Apparao et al., Indian J. Chem., Sect. B., 23(1): 15-17 (1984)).
Database Beilstein [Online] Beilstein Institute for Organic Chemistry, Frankfurt-Main, DE; Database accession No. 8216060 (BRN) abstract (Ma et al., J. Am. Chem. Soc., 120(48): 12459-12467 (1998)).
Database Beilstein [Online] Beilstein Institute for Organic Chemistry, Frankfurt-Main, DE; Database accession No. 194433, 1468537, 1470883 (BRNs) abstract (Grigoryan, Agbalyan, Khim, Geteroisikl. Soedin., 15: 384-351 (1979)).
Database Beilstein [Online] Beilstein Institute for Organic Chemistry, Frankfurt-Main, DE; Database accession No. 2100509 (BRN) abstract (Huffman, et al., J. Org. Chem., 34(8): 2407-2414, 1969)).
Database Beilstein [Online] Beilstein Institute for Organic Chemistry, Frankfurt-Main, DE; Database accession No. 5545033 (BRN) abstract (Heinicke et al., Aust. J. Chem., 37(4): 831-844 (1984).
Database Beilstein [Online] Beilstein Institute for Organic Chemistry, Frankfurt-Main, DE; Database accession No. 4692231 (BRN) abstract (Kamath et al., Indian J. Chem., Sect. B, 21(10): 911-913 (1982).
Database Beilstein [Online] Beilstein Institute for Organic Chemistry, Frankfurt-Main, DE; Database accession No. 1, 5813745 (BRN) abstract (Upton, J. Chem. Res. Miniprint, 4: 0951-0965 (1992).

(Continued)

*Primary Examiner* — Kamal Saeed
*Assistant Examiner* — Kristin Bianchi
(74) *Attorney, Agent, or Firm* — Rothwell, Figg, Ernst & Manbeck PC

(57) ABSTRACT

This invention is directed to substituted aryl compounds, which are linked to a substituted indole moiety by various linkers, and the kynurenine/kynuramine-like metabolites of these agents, their preparation and pharmaceutical compositions containing these compounds. This invention further is directed to the pharmaceutical use of the compounds for inhibiting GSK3β kinase and/or modulating N-methyl-D-aspartate (NMDA) channel activities for the treatment of neurodegenerative and other disorders.

9 Claims, No Drawings

OTHER PUBLICATIONS

Database Beilstein [Online] Beilstein Institute for Organic Chemistry, Frankfurt-Main, DE; Database accession No. 3297567 (BRN) abstract (De Diesbach, Helv. Chim. Acta, 24: 158-166 (1941).

Database Beilstein [Online] Beilstein Institute for Organic Chemistry, Frankfurt-Main, DE; Database accession No. 3296010 (BRN) abstract (Tanasescu, et al., Bull. Soc. Chim. Fr., pp. 234-238 (1932).

Database Beilstein [Online] Beilstein Institute for Organic Chemistry, Frankfurt-Main, DE; Database accession No. 192254 (BRN) abstract (Katritzky, J. Chem. Soc. pp. 2586-2591 (1955).

Database Beilstein [Online] Beilstein Institute for Organic Chemistry, Frankfurt-Main, DE; Database accession no. 435020 (BRN) abstract (Leonard, Lambert, J. Org. Chem., 34: 3240-3248 (1969).

De Sarno, et al., "In vivo regulation of GSK3 phosphorylation by cholinergic and NMDA receptors," Neurobiology of Aging, 27(3): 413-422 (Mar. 1, 2006).

Kulagowski, et al., "Glycine-Site NMDA Receptor Antagonists," Expert Opinion on Therapeutic Patents, 5(10): 1061-1075 (Jan. 1, 1995).

Alonso, et al., "GSK-3 Inhibitors: Discoveries and Developments," Current Medicinal Chemistry, 11(6): 755-763(Mar. 1, 2004).

Meijer et al., "Pharmacological inhibitors of glycogen synthase kinase 3," Trends in Pharmacological Sciences, 25(9): 471-480 (Sep. 1, 2004).

International Search Report and the Written Opinion of the International Searching Authority for PCT/IB2007/004306, dated Jun. 19, 2008.

K. Görlitzer, et al., "10H-Indolo[3,2-b]chinoline," Archiv der Pharmazie, vol. 314, No. 10, Oct. 1981, 12 pages.

Lala et al., Role of nitric oxide in tumor progression: Lessons from experimental tumors, Cancer and Metastasis Reviews (1998), 17, 91-106.

Golub et al., Molecular Classification of Cancer: Class Discovery and Class Prediction by Gene Expression Monitoring, Science (1999), vol. 286, 531-537.

"Anxiety," [retrieved on May 14, 2008]. Retrieved online via Internet, URL: http://www.nlm.nih.gov/medlineplus/anxiety.html#cat3.

SUBSTITUTED ARYL-INDOLE COMPOUNDS AND THEIR KYNURENINE/KYNURAMINE-LIKE METABOLITES AS THERAPEUTIC AGENTS

This application is a continuation of U.S. Ser. No. 12/611,373 filed Nov. 3, 2009, now U.S. Pat. No. 8,003,702 which is a divisional of U.S. Ser. No. 11/865,437 filed Oct. 1, 2007, now U.S. Pat. No. 7,622,495 which claims priority from U.S. Provisional application Ser. No. 60/848,642, filed Oct. 3, 2006. These prior applications are incorporated herein by reference.

FIELD OF THE INVENTION

The present invention relates to a novel family of substituted aryl compounds, pharmaceutical formulations containing them, use of the compounds in the manufacture of medicaments for treating various diseases, and methods of treating these diseases.

BACKGROUND OF THE INVENTION

The present invention relates to novel compounds for inhibiting glycogen synthase kinase-3 (GSK3β) and/or modulators of NMDA channel activities and their use in regulating biological conditions mediated by GSK3β activity and or NMDA channel activity and, more particularly, to the use of such compounds in the treatment of biological conditions such as neurodegenerative diseases, type II diabetes, cancer and affective disorders. The present invention further relates to methods of treating neurodegenerative disorders using GSK3β inhibitors and NMDA modulators.

Synonyms for GSK3β include Tau protein kinase I (TPK I), FA (Factor A) kinase, kinase FA and ATP-citrate lyase kinase (ACLK). GSK3 exists in two isoforms, i.e. GSK3α and GSK3β, and is a proline-directed serine/threonine kinase originally identified as an enzyme that phosphorylates glycogen synthase. However, it has been demonstrated that GSK3β phosphorylates numerous proteins in vitro such as glycogen synthase, phosphatase inhibitor 1-2, the type-II subunit of cAMP-dependent protein kinase, the G-subunit of phosphatase-1, ATP-citrate lyase, acetyl coenzyme A carboxylase, myelin basic protein, a microtubule-associated protein, a neurofilament protein, an N-CAM cell adhesion molecule, nerve growth factor receptor, c-Jun transcription factor, JunD transcription factor, c-Myb transcription factor, c-Myc transcription factor, L-Myc transcription factor, adenomatous polyposis coli tumor suppressor protein, Tau protein and β-catenin.

GSK3β inhibitors may act to increase the survival of neurons subjected to aberrantly high levels of excitation induced by the neurotransmitter glutamate (Nonaka, S., et al., *Proc. Natl. Acad. Sci. USA*, 95(3):2642-7, 1998). Glutamate-induced neuronal excitotoxicity is also believed to be a major cause of neurodegeneration associated with acute damage, such as in cerebral ischemia, traumatic brain injury and bacterial infection. Furthermore, it is believed that excessive glutamate signaling is a factor in the chronic neuronal damage seen in diseases such as Alzheimer's, Huntington's, Parkinson's, AIDS associated dementia, amyotrophic lateral sclerosis (ALS) and multiple sclerosis (MS) (Thomas, R J., *J. Am. Geriatr Soc.*, 43:1279-89, 1995.

N-methyl-D-aspartate receptors are critical for neuronal plasticity and survival, whereas their excessive activation produces excitotoxicity and may accelerate neurodegeneration. Stimulation of NMDARs in vitro (cultured rat hippocampal or cortical neurons) and in the adult mouse brain in vivo disinhibited GSK3S via protein phosphatase 1(PP1)-mediated dephosphorylation of GSK3β at the serine 9 residue (Szatmari, E., et al, *J. Biol. Chem.*, 280(11):37526-35, 2005). NMDA-triggered GSK3β activation was mediated by NMDAR that contained the NR2B subunit. These data suggest existence of a feedback loop between GSK3β and PP1 that results in amplification of PP1 activation by GSK3β. The excessive activation of NR2B-PP1-GSK3β-PP1 circuitry may contribute to the neurodegeneration induced by excessive NMDA. GSK3R inhibitors might mimic the action of certain hormones and growth factors, such as insulin, which use the GSK3β pathway.

GSK3β is considered to be an important player in the pathogenesis of Alzheimer's disease. GSK-3 was identified as one of the kinases that phosphorylate Tau, a microtubule-associated protein, which is responsible for the formation of paired helical filaments (PHF), an early characteristic of Alzheimer's disease. Apparently, abnormal Tau hyperphosphorylation is the cause for destabilization of microtubules and PHF formation. Consequently, GSK-3 inhibitors are believed to be potentially useful for treatment of these and other neurodegenerative disorders. Indeed, disregulation of GSK-3 activity has been recently implicated in several CNS disorders and neurodegenerative diseases, including schizophrenia (Beasley, C., et al., *Neurosci Lett.*, 302(20):117-20, 2001; Kozlovsky, N., et al., *Eur. Neuropsychopharmacol*, 12:13-25, 2002), stroke, and Alzheimer's disease (AD) (Ghat, R. V. and Budd, S. L., *Neurosignals*, 11:251-61, 2002; Hernandez, F., et al., *J. Neurochem.*, 83:1529-33, 2002; Lucas, J. J., et al., *EMBO J*, 20:15):27-39, 2001; Mandelkow, E. M., et al., *FEBS Lett.*, 314(21):315-21, 1992).

It thus would be desirable to provide a class of GSK3β inhibitors that would be useful in the treatment of diseases mediated through GSK3β activity such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Down syndrome, myotonic dystrophy, Parkinson's Disease, Amyotrophic Lateral Sclerosis (ALS), Parkinsonism-dementia complex of Guam, AIDS related dementia, Postencephalic Parkinsonism, prion diseases with tangles, subacute sclerosing panencephalitis, frontal lobe degeneration (FLD), argyrophilic grains disease, subacute sclerotizing panencephalitis (SSPE) (late complication of viral infections in the central nervous system), inflammatory diseases, cancer, dermatological disorders such as baldness, neuronal damage, schizophrenia, pain, in particular neuropathic pain. GSK3β inhibitors can also be used to inhibit sperm motility and can therefore be used as male contraceptives.

Ions such as glutamate play a key role in processes related to chronic pain and neurotoxicity, primarily by acting through N-methyl-D-aspartate receptors. Thus, inhibition of such action, by employing ion channel antagonists or negative modulators, can be beneficial in the treatment and control of CNS diseases. NMDA receptor activity produces synaptic plasticity in the central nervous system that affects processes for learning and memory, including long-term potentiation and long-term depression (Dingledine R., *Crit. Rev. Neurobiol.*, 4(1):196, 1988). However, prolonged activation of NMDA receptor under pathological conditions (such as cerebral ischemia and traumatic injury) causes neuronal cell death (Rothman S. M. and Olney J. W., *Trends Neurosci.*, 18(2):57 8, 1995). NMDA receptor-mediated excitotoxicity may contribute to the etiology or progression of several neurodegenerative diseases, such as Parkinson's disease and Alzheimer's disease. Since open channel blockers of NMDA receptors were shown, in the late 1980s, to have potential for therapy of ischemic stroke, the receptor has been considered an attractive therapeutic target for the development of neuroprotective agents. Unfortunately, the development of these compounds as neuroprotectants is often limited by their psychiatric side-effects associated with their undesired pharmacodynamic properties such as slow dissociation from the receptor (Muir K. W. and Lees K. R., *Stroke*, 26(3):503 13, 1995).

Known NMDA antagonists include ketamine, dextromophan, and 3-(2-carboxypiperazin-4-yl)-propyl-1-phosphonic acid ("CPP"). Although these compounds have been reported (J. D. Kristensen, et al., *Pain*, 51:249 253 (1992); P. K. Eide, et al., *Pain*, 61:221 228 (1995); D. J. Knox, et al., *Anaesth. Intensive Care* 23:620 622 (1995); and M. B. Max, et al., *Clin. Neuropharmacol.* 18:360 368 (1995)) to produce symptomatic relief in a number of neuropathies including postherpetic neuralgia, central pain from spinal cord injury, and phantom limb pain, widespread use of these compounds is precluded by their undesirable side effects. Such side effects at analgesic doses include psychotomimetic effects such as dizziness, headache, hallucinations, dysphoria, and disturbances of cognitive and motor function. Additionally, more severe hallucinations, sedation, and ataxia are produced at doses only marginally higher than analgesic doses. Thus, it would be desirable to provide novel NMDA modulators that are absent of undesirable side effects or that produce fewer and/or milder side effects.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2c and NR2D. Ishii, T., et al., *J. Biol. Chem.*, 268:2836-2843 (1993), and Laurie, D. J., et al., *Mol. Brain. Res.*, 51:23-32 (1997) describe how the various resulting combinations produce a variety of NMDA receptors differing in physiological and pharmacological properties such as ion gating properties, magnesium sensitivity, pharmacological profile, as well as in anatomical distribution.

SUMMARY OF THE INVENTION

The invention relates to compounds and their salts having the formula (I):

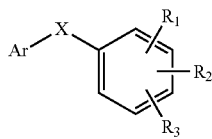

wherein
each $R_1$, $R_2$ and $R_3$ independently is selected from hydrogen, carboxy, nitro, $C_1$-$C_4$ alkylsulfonyl, aminosulfonyl, $C_1$-$C_4$ alkyl aminosulfonyl, halogen, cyano, $C_{1-4}$ alkyl, $C_{1-4}$ alkoxy, NR'R", aryl, aryl-$C_{1-4}$ alkyl, or aryl-$C_{1-4}$ alkoxy, and each of R' and R" is independently H or $C_{1-4}$ alkyl, or R'=R"=ClCH$_2$CH$_2$, or NR'R" constitutes a saturated heterocyclic ring containing 3-8 ring members;

X is:

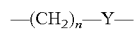

wherein Y is: >NH, >C=O, >C=S or none; n is 0-4; any carbon of the —(CH$_2$)$_n$— may be substituted by 1-2 substituents independently selected from among halogen, carboxy, $C_{1-4}$alkyl, $C_{1-4}$ alkoxy, OH, NH$_2$ or acyl,
Ar is a kynurenine/kynuramine metabolite of a 3-indole:

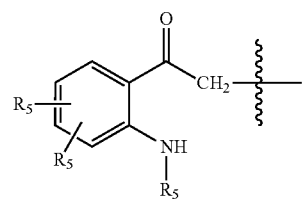

or a 3-indole:

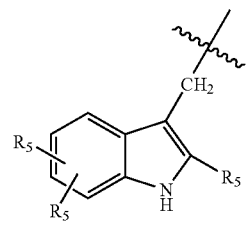

wherein each $R_5$ independently is hydrogen, halogen, $C_{1-4}$ alkyl, $C_{1-4}$, alkoxy, OH, NR'R" as defined above, nitro, aryl, aryl-$C_{1-4}$ alkyl, or aryl-$C_{1-4}$ alkoxy;
with the provisos that:
if X is —(CH$_2$)$_2$—NH—, Ar is 3-indole, $R_1$ is 4-methylsulfonyl and $R_3$ and each $R_5$ is hydrogen, then $R_2$ cannot be 2-nitro;
if X is unsubstituted —(CH$_2$)$_2$—NH—, Ar is 3-indole, $R_1$ is 4-nitro and $R_3$ and each $R_5$ is hydrogen, then $R_2$ cannot be 2-bromo;
if X is substituted or unsubstituted —(CH$_2$)$_2$—NH— and Ar is 3-indole or 2-aminobenzoyl, then $R_1$ and $R_2$ cannot be 2,4-dinitro;
and if X is unsubstituted —(CH$_2$)$_2$—NH—, Ar is 3-indole, an $R_5$ is 5-methoxy, then $R_1$ and $R_2$ cannot be 2,4-dinitro.

In another aspect, the invention provides a pharmaceutical formulation that comprises at least one pharmaceutically acceptable diluent, preservative, solubilizer, emulsifier, adjuvant, and/or carrier, and at least one member of the group consisting of the compounds of the invention as defined above and pharmaceutically acceptable salts thereof.

In yet another aspect, the invention comprises the administration of an effective amount of at least one of the compounds of the invention as defined above and pharmaceutically acceptable salts thereof, for the prevention or treatment of a disease, disorder or biological condition which is mediated by GSK3β activity or NMDA channel activity or associated with excess GSK3β or NMDA activity.

DETAILED DESCRIPTION OF THE INVENTION

Compounds of the present invention are based on indole and its metabolites. The amino acid tryptophan and other indole derivatives such as melatonin are converted biologically through the "kynurenine pathway" (Beadle, G. W., et al., *Proc. Natl. Acad. Sci. USA*, 33:155-8, 1947, see Heidelberger, C., et al., *J. Biol. Chem.*, 179:143, 1949). Over 95% of all dietary tryptophan is metabolized to kynurenines (Wolf, H., *J. Clin. Lab. Invest.*, 136(Suppl):1-86, 1974). In peripheral tissues, particularly the liver, the indole ring of tryptophan or melatonin is modified by either tryptophan dioxygenase or indoleamine 2,3-dioxygenase, which results in the formation of formylkynurenine or N1-acetyl-N2-formyl-5-methoxykynuramine (AFMK), respectively. Formylase then rapidly converts formylkynurenine to L-kynurenine which is the key compound in the kynurenine pathway (Mehler & Knox 1950) and AFMK to N1-acetyl-5-methoxykynuramine (AMK).

The invention relates to compounds and their salts having the formula (I):

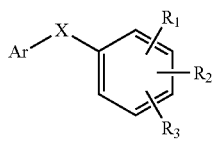

wherein each of $R_1$, $R_2$ and $R_3$ independently is selected from hydrogen, carboxy, nitro, $C_1$-$C_4$ alkylsulfonyl, aminosulfonyl, $C_1$-$C_4$ alkyl aminosulfonyl, halogen, cyano, $C_{1-4}$ alkyl, $C_{1-4}$ alkoxy, NR'R", aryl, aryl-$C_{1-4}$ alkyl, or aryl-$C_{1-4}$ alkoxy, and each of R' and R" is independently H or $C_{1-4}$ alkyl, or R'=R"=ClCH$_2$CH$_2$, or NR'R" constitutes a saturated heterocyclic ring containing 3-8 ring members;

X is:

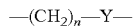

wherein Y is: >NH, >C=O, >C=S or none; n is 0-4; any carbon of the —(CH$_2$)$_n$— may be substituted by 1-2 substituents independently selected from among halogen, carboxy, $C_{1-4}$ alkyl, $C_{1-4}$ alkoxy, OH, NH$_2$ or acyl, Ar is a 3-indole:

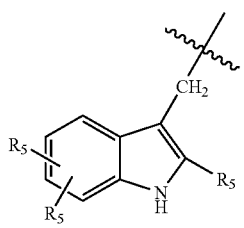

or a kynurenine/kynuramine metabolite thereof:

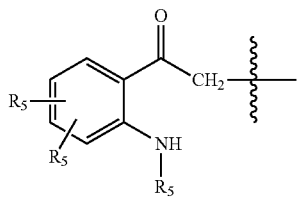

wherein each $R_5$ independently is hydrogen, halogen, $C_{1-4}$ alkyl, $C_{1-4}$ alkoxy, OH, NR'R" as defined above, nitro, aryl, aryl-$C_{1-4}$ alkyl, or aryl-$C_{1-4}$ alkoxy; with the provisos that:

if X is —(CH$_2$)$_2$—NH—, Ar is 3-indole, $R_1$ is 4-methylsulfonyl and $R_3$ and each $R_5$ is hydrogen, then $R_2$ cannot be 2-nitro;

if X is unsubstituted —(CH$_2$)$_2$—NH—, Ar is 3-indole, $R_1$ is 4-nitro and $R_3$ and each $R_5$ is hydrogen, then $R_2$ cannot be 2-bromo; and if X is substituted or unsubstituted —(CH$_2$)$_2$—NH— and Ar is 3-indole or 2-aminobenzoyl, then $R_1$ and $R_2$ cannot be 2,4-dinitro;

and if X is unsubstituted —(CH$_2$)$_2$—NH—, Ar is 3-indole, an $R_5$ is 5-methoxy, then $R_1$ and $R_2$ cannot be 2,4-dinitro.

In preferred embodiments, Y is >NH, each of $R_1$, $R_2$ and $R_3$ is independently selected from hydrogen, carboxy, nitro, $C_1$-$C_4$ alkylsulfonyl, halogen and cyano, and each $R_5$ independently is selected from hydrogen and $C_{1-4}$ alkoxy.

Preferred compounds within the generic class of compounds set forth above include 2-(2-aminobenzoyl)-N-2-nitro-4-methylsulfonyl-phenylethylamine; N-(4-methylsulfonyl-2-nitrophenyl)-5-methoxytryptamine; N-(2-bromo-4-nitrophenyl)-5-methoxytryptamine; N-(4-bromo-2-nitrophenyl)-5-methoxytryptamine; N-(2-cyano-4-nitrophenyl)-5-methoxytryptamine; 2-(2-aminobenzoyl)-N-2-bromo-4-nitro-phenylethylamine; 2-(2-aminobenzoyl)-N-2-nitro-4-bromo-phenylethylamine; 2-(2-aminobenzoyl)-N-2-nitro-4-cyano-phenylethylamine; N-(2-nitrophenyl)-tryptamine; N-(4-carboxy-2-nitrophenyl)-tryptamine; N-(2-carboxy-4-nitrophenyl)-tryptamine; N-(2-nitrophenyl)-5-methoxytryptamine; N-(4-carboxy-2-nitrophenyl)-5-methoxytryptamine; N-(2-carboxy-4-nitrophenyl)-5-methoxytryptamine; N-(2-cyano-4-nitrophenyl)-tryptamine; N-(2-nitro-4-bromophenyl)-tryptamine, N-(3,4-dicyanophenyl)-tryptamine, N-(3,4-dicyanophenyl)-5-methoxytruptamine and 2-(2-aminobenzoyl)-N-2-nitrophenylethylamine.

Particularly preferred compounds include N-(4-methylsulfonyl-2-nitrophenyl)-5-methoxytryptamine; N-(2-nitrophenyl)-5-methoxytryptamine; N-(2-cyano-4-nitrophenyl)-tryptamine; 2-(2-aminobenzoyl)-N-2-nitro-4-methylsulfonyl-phenylethylamine; and N-(2-nitrophenyl)-tryptamine.

In another aspect, the invention provides a pharmaceutical formulation that comprises at least one pharmaceutically acceptable diluent, preservative, solubilizer, emulsifier, adjuvant, and/or carrier, and at least one member of the group consisting of the compounds of the invention as defined above and pharmaceutically acceptable salts thereof.

A pharmaceutical formulation according to the invention is preferably characterized by at least one of the following features:

(i) it is adapted for oral, rectal, parenteral, transbuccal, topical, intrapulmonary (e.g. by inhalation), intranasal or transdermal administration;

(ii) it is in unit dosage form, each unit dosage comprising an amount of at least one compound of formula (I) which is within the range of about 0.001-about 100 mg/kg;

(iii) it is a controlled release formulation, wherein at least one compound of formula (I) is released at a predetermined controlled rate.

The amount of a compound of formula (I) useful in treating a disease or disorder can vary with the nature and severity of the condition to be treated, the particular method of administration selected, the frequency of administration, the age, sex, weight and general condition of the patient and other factors evident to those of skill in the art. Generally, if the unit dosage is to be administered orally, a dose within the range of about 0.01 mg/kg-about 50 mg/kg daily, preferably within the range of about 0.05 mg-about 10 mg/kg, is effective. A more preferred dosage for oral administration is within the range of about 0.5-about 10 mg/kg daily. If the compound is to be administered parenterally or transdermally, a unit dosage within the range of about 0.005-about 15 mg/kg generally is desirable.

For oral administration, the pharmaceutical formulations may be utilized as, e.g., tablets, orally disintegrating tablets, capsules, emulsions, solutions, syrups or suspensions. For parenteral administration, the formulations can be utilized as ampoules, or otherwise as suspensions, solutions or emulsions in aqueous or oily vehicles. The need for suspending, stabilizing and/or dispersing agents will, of course, take account of the fact of the solubility or otherwise of the active compounds, in the vehicles that are used in the particular embodiments. The formulations additionally can contain physiologically compatible preservatives and antioxidants. In the formulations for topical application, e.g. creams, lotions or pastes, the active ingredient can be mixed with conventional oleaginous or emulsifying excipients.

The pharmaceutical formulations also can be utilized as suppositories with conventional suppository bases such as cocoa butter or other glycerides. Alternatively, the formulations can be made available in a depot form, which will release the active composition slowly in the body, over a pre-selected time period.

The compounds of the invention also can be administered by using conventional transbuccal, intranasal, intrapulmonary or transdermal delivery systems.

The compounds of formula (I) or their salts can be administered in combination with other therapeutic agents, especially compounds that act as anxiolytics, tranquilizers, analgesics, mood stabilizers, anti-Parkinson's agents (dopaminergic and non-dopaminergic drugs), anti-Alzheimer's drugs or anti-diabetic agents. "In combination" as used herein is intended to mean either that the compounds of the invention are physically combined with one or more additional therapeutic agents or that they are administered in separate physical forms but sufficiently close in time that both act within the body within a given time period. Examples of suitable anxiolytics which can be administered in combination with the compounds of formula I include flunitrazepam, diazepam and alprazolam; suitable tranquilizers include clonazepam, zolpidem, trazodone and melatonin; suitable analgesics include aspirin, ibuprofen and diclofenac; suitable mood stabilizers include lithium, sodium valproate and carbamazepine; suitable anti-Parkinon's agents include levodopa/carbidopa, cabergolline, pergolide, pramipexole, ropinirol, entacapone (COMT inhibitor), selegiline and rasagiline (MAO-B inhibitors); and suitable anti-diabetic agents include metformin, acarbose and glipizide. These known therapeutic agents can be physically combined with the compounds of the present invention or administered in combination with the compounds of the present invention but in separate physical form.

The compounds of formula I and their salts are administered to inhibit GSK3β activity or NMDA channel activity in animals or humans. More particularly, the compounds can be administered to prevent or to treat diseases, disorders or conditions which are mediated through GSK3β activity or NMDA channel activity or associated with excess GSK3β activity or NMDA channel activity. Such diseases, disorders and conditions, include central nervous system (CNS) disorders and traumas and neurodegenerative diseases, such as bipolar disorder (particularly manic-depressive disorder), Alzheimer's disease, Parkinson's disease, FTDP-17 (frontaltemporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Parkinsonism-dementia complex of Guam, AIDS-related dementia, postencepalic Parkinsonism, prion diseases with tangles, Amyotrophic Lateral Sclerosis (ALS) subacute sclerosing panencephalitis, frontal lobe degeneration (FLD), argyrophilic grains disease, subacute sclerotizing panencephalitis (SSPE) (late complication of viral infections in the central nervous system), neuronal damage and schizophrenia; diabetes; leukopenia; Down Syndrome; myotonic dystrophy; inflammatory diseases; cancer and other proliferative disorders; dermatological disorders, such as baldness; cancer; pain, including neuropathic pain and chronic pain; migraines, psychiatric diseases, such as depression; anxiety; and stroke.

The invention is further illustrated by the following examples which are provided for illustrative purposes only and are not intended to be limiting.

EXAMPLE 1

2-(2-aminobenzoyl)-N-2-nitro-4-methylsulfonyl-phenylethylamine

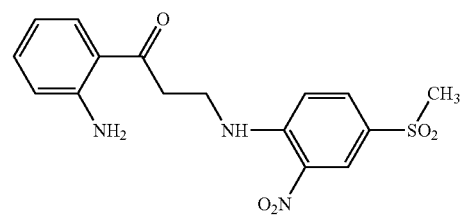

General procedure for the synthesis of 2-(2-aminobenzoyl)-N-2-nitro-4-methylsulfonyl-phenylethylamine In a 100 ml three-necked round-bottom flask kept under an argon atmosphere, 250 mg (1.14 mmoles, 1 eq) of methyl-4-fluoro-3-nitrobenzensulfone were dissolved in 20 ml of ethanol. Kynuramine dihydrobromide 371 mg (1 eq) was then added under magnetic stirring in one portion. After 15 minutes $Na_2CO_3$ 326 mg (3 eq) was added to the reaction.

The reaction course was followed by HPLC-MS that, after 6 hours, showed complete conversion. The yellow precipitate was then collected by filtration, washed with water and cold EtOH and then dried under vacuum at 40° C.

The desired product was recovered as a yellow solid (300 mg). 1H NMR (DMSO-$d_6$, 400 MHz) δ 3.20 (s, 3H, $SO_2CH_3$), 3.38 (br t, J=6.8 Hz, 2H, $NHCH_2CH_2$), 3.77-3.81 (m, 2H, $NHCH_2CH_2$), 6.51-6.55 (m, 1H, aromatic H), 6.76 (dd, $J_1$=1.2 Hz, $J_2$=8.4 Hz, 1H, aromatic H), 7.22-7.27 (m, 3H, 1 aromatic H+$NH_2$), 7.35 (d, J=9.6 Hz, 1H, aromatic H), 7.76 (dd, $J_1$=1.4 Hz, $J_2$=8.4 Hz, 1H, aromatic H), 7.92 (dd, $J_1$=2.1 Hz, $J_2$=9.0 Hz, 1H, aromatic H), 8.49 (d, J=2.1 Hz, 1H, aromatic H), 8.72 (br t, J=5.9 Hz, 1H, $NHCH_2CH_2$).

EXAMPLE 2

N-(4-methylsulfonyl-2-nitrophenyl)-5-methoxytryptamine

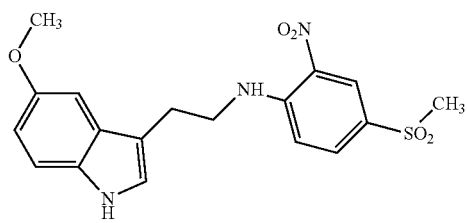

General procedure for the synthesis of N-(4-methylsulfonyl-2-nitrophenyl)-5-methoxytryptamine In a 100 ml three-necked round-bottom flask kept under an argon atmosphere, 483 mg (2.20 mmoles, 1eq) of methyl-4-fluoro-3-nitrobenzensulfone were dissolved in 40 ml of ethanol. 5-methoxytryptamine hydrochloride 500 mg (1eq) was then added under magnetic stirring in one portion. After 15 minutes $Na_2CO_3$ 466 mg (2 eq) was added to the reaction. The reaction was heated to 50° C. using an oil bath. The reaction course was followed by HPLC-MS that, after 3 hours, showed complete conversion. The orange precipitate was collected by filtration, washed with water and cold EtOH and then dried under vacuum at 40° C. The desired product was recovered as an orange solid (350 mg).

$^1$H NMR (DMSO-$d_6$, 400 MHz) δ 3.05 (t, J=7.1 Hz, 2H, $NHCH_2CH_2$), 3.20 (s, 3H, $SO_2CH_3$), 3.71-3.75 (m, 5H, $OCH_3$+$NHCH_2CH_2$), 6.71 (dd, $J_1$=2.6 Hz, $J_2$=8.8 Hz, 1H, aromatic H), 7.07 (d, J=2.4 Hz, 1H, aromatic H), 7.22-7.24 (m, 2H, aromatic H), 7.28 (d, J=9.0 Hz, 1H, aromatic H), 7.89 (dd, $J_1$=2.0 Hz, $J_2$=8.9 Hz, 1H, aromatic H), 8.47 (d, J=2.6 Hz, 1H, aromatic H), 8.64 (br t, J=5.7 Hz, 1H, $NHCH_2CH_2$) 10.73 (br s, 1H, NH).

EXAMPLE 3

N-(2-bromo-4-nitrophenyl)-5-methoxytryptamine

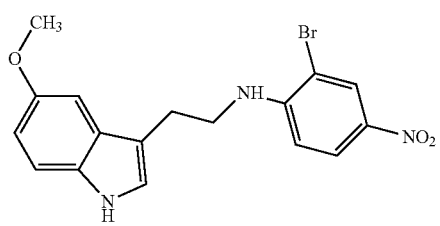

EXAMPLE 4

N-(4-bromo-2-nitrophenyl)-5-methoxytryptamine

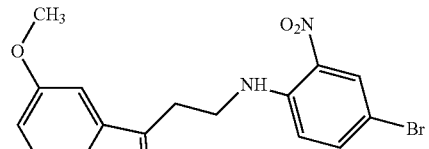

EXAMPLE 5

N-(2-cyano-4-nitrophenyl)-5-methoxytryptamine

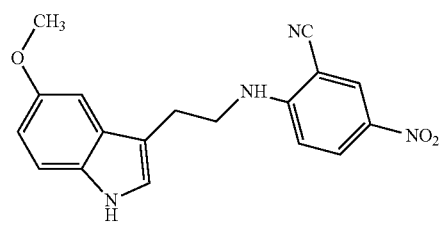

General procedure for the synthesis of N-(2-bromo-4-nitrophenyl)-5-methoxytryptamine, N-(4-bromo-2-nitrophenyl)-5-methoxytryptamine and N-(2-cyano-4-nitrophenyl)-5-methoxytryptamine 1 equivalent of 1-fluoro-$2R_1$-$4R_2$-benzene was reacted in ethanol, at room temperature, with 1 equivalent of 5-methoxytryptamine, to yield the desired product, as follows:

(N-(2-bromo-4-nitrophenyl)-5-methoxytryptamine):
  $R_1$=Br, $R_2$=$NO_2$; reaction time 3 h; yield referred to chromatographed product: 70%

(N-(4-bromo-2-nitrophenyl)-5-methoxytryptamine):
  $R_1$=$NO_2$, $R_2$=Br; reaction time 3 h; yield referred to isolated product (collected by filtration): 50%

N-(2-cyano-4-nitrophenyl)-5-methoxytryptamine):
  $R_1$=CN, $R_2$=$NO_2$; reaction time 3 h; yield referred to isolated product (collected by filtration): 50%

NMR spectra of compounds N-(2-bromo-4-nitrophenyl)-5-methoxytryptamine, N-(4-bromo-2-nitrophenyl)-5-methoxytryptamine and N-(2-cyano-4-nitrophenyl)-5-methoxytryptamine N-(2-bromo-4-nitrophenyl)-5-methoxytryptamine $^1$H NMR (DMSO-$d_6$, 400 MHz) δ 2.96 (t, J=7.7 Hz, 2H, $CH_2$), 3.54-3.59 (m, 2H, $CH_2$—NH), 3.74 (s, 3H, $OCH_3$), 6.62 (br t, J=5.8 Hz, 1H, $CH_2$—NH), 6.70 (dd, $J_1$=2.5 Hz, $J_2$=8.7 Hz, 1H, aromatic H), 6.83 (d, J=9.2 Hz, 1H, aromatic H), 7.03 (d, J=2.2 Hz, 1H, aromatic H), 7.18-7.22 (m, 2H, aromatic H), 8.04 (dd, $J_1$=2.2 Hz, $J_2$=9.2 Hz, 1H, aromatic H), 8.25 (d, J=2.5 Hz, 1H, aromatic H), 10.69 (br s, 1H, NH).

N-(4-bromo-2-nitrophenyl)-5-methoxytryptamine $^1$H NMR (DMSO-$d_6$, 400 MHz) δ 3.01 (t, 2H, J=6.9 Hz, CH$_2$), 3.59-3.64 (m, 2H, CH$_2$—NH), 3.73 (s, 3H, OCH$_3$), 6.70 (dd, $J_1$=2.8 Hz, $J_2$=8.7 Hz, 1H, aromatic H), 7.03-7.07 (m, 2H, aromatic H), 7.19-7.22 (m, 2H, aromatic H), 7.60 (dd, $J_1$=2.1 Hz, $J_2$=9.6 Hz, 1H, aromatic H), 8.11 (d, J=2.8 Hz, 1H, aromatic H), 8.20 (br t, J=5.6 Hz, 1H, CH$_2$—NH), 10.71 (br s, 1H, NH).

N-(2-cyano-4-nitrophenyl)-5-methoxytryptamine $^1$H NMR (DMSO-$d_6$, 400 MHz) δ 2.97 (t, 2H, J=7.4 Hz, CH$_2$), 3.58-3.63 (m, 2H, CH$_2$—NH), 3.76 (s, 3H, OCH$_3$), 6.71 (dd, $J_1$=2.5 Hz, $J_2$=8.8 Hz, 1H, aromatic H), 6.93 (d, J=9.6 Hz, 1H, aromatic H), 7.04 (d, J=2.2 Hz, 1H, aromatic H), 7.17-7.23 (m, 2H, aromatic H), 7.59 (br t, J=6.0 Hz, 1H, CH$_2$—NH), 8.15 (dd, $J_1$=3.0 Hz, $J_2$=9.4 Hz, 1H, aromatic H), 8.41 (d, J=2.9 Hz, 1H, aromatic H), 10.70 (br s, 1H, NH).

EXAMPLE 6

2-(2-aminobenzoyl)-N-2-bromo-4-nitro-phenylethylamine

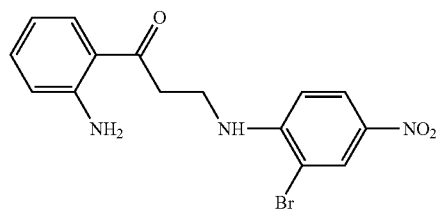

EXAMPLE 7

2-(2-aminobenzoyl)-N-2-nitro-4-bromo-phenylethylamine

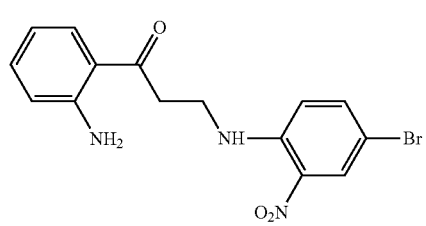

EXAMPLE 8

2-(2-aminobenzoyl)-N-2-nitro-4-cyano-phenylethylamine

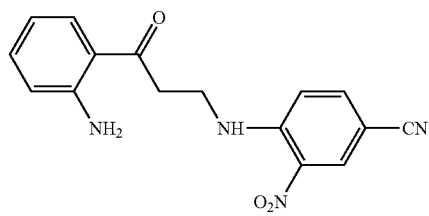

General procedure for the synthesis of 2-(2-aminobenzoyl)-N-2-bromo-4-nitro-phenylethylamine, 2-(2-aminobenzoyl)-N-2-nitro-4-bromo-phenylethylamine and 2-(2-aminobenzoyl)-N-2-nitro-4-cyano-phenylethylamine 3×125 mg (3×1 equiv) of kynuramine dihydrobromide were dissolved under an argon atmosphere in 3×1 ml of absolute ethanol in three different flasks of a Carousel parallel synthesizer. Triethylamine (3×0.1 ml, 3×2 equiv) was also added in each flask. 2-Bromo-1-fluoro-4-nitrobenzene (85 mg, 1 equiv), 4-bromo-1-fluoro-2-nitrobenzene (85 mg, 1 equiv) and 2-fluoro-5-nitrobenzonitrile (65 mg, 1 equiv) were then added respectively in one of the three parallel flasks (A, B and C) and the obtained mixtures were allowed to react at room temperature under magnetic stirring. The course of the reactions was followed by TLC (dichloromethane as the eluent). Reactions A, B and C were all completed after 16 hours. The three reaction mixtures were then concentrated under reduced pressure and the resulting residues were purified by column chromatography on silica gel (approx. 10 grams) by using dichloromethane as the eluent.

2(2-aminobenzoyl)-N-2-bromo-4-nitro-phenylethylamine was obtained as a yellow solid in 30% yield, 2(2-aminobenzoyl)-N-2-nitro-4-bromo-phenylethylamine was collected as an orange solid in 40% yield and 2(2-aminobenzoyl)-N-2-nitro-4-cyano-phenylethylamine was isolated as a yellow solid in 40% yield.

EXAMPLE 9

N-(2-Nitrophenyl)-tryptamine

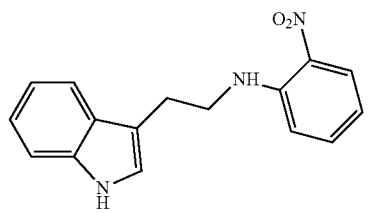

Procedure:
In a 250 ml round bottom flask DMF (1 eq.), tryptamine (1 eq.), 2-nitrofluorobenzene (1 eq.) were taken and stirred for 10 min. Then potassium carbonate (1.1 eq.) was added at room temperature. The stirring was continued for 2 hours.

TLC was monitored. The reaction mixture was poured into ice water and stirred for 15 min. The resultant solid was filtered and washed with water. The crude material was crystallized from methanol. The yield was 60%.

NMR: (CDCl$_2$) δ 3.2 (t, 2H, CH$_2$), 3.6 (t, 2H, CH$_2$NH), 6.6 (t, 1H, 4'-H), 6.8 (d, 1H, 7-H), 7.1-7.3 (m, 3H, 2-H, 5-H, 6-H), 7.4 (m, 2H, 4-H, 6'-H), 7.6 (d, 1H, 5'-H) 8.1 (m, 3H, 3'-H, 2×NH).

EXAMPLE 10

N-(4-Carboxy-2-nitrophenyl)-tryptamine

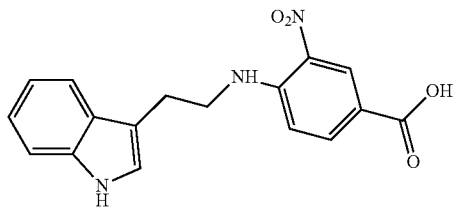

Procedure:

In a 250 ml round bottom flask DMF (10 eq.), tryptamine (1 eq.), and 4-carboxy-2-nitrofluorobenzene (1 eq.) were added and stirred for 10 min. Then potassium carbonate (2.5 eq.) was added at room temperature. The stirring was continued for 2 hrs. TLC was monitored. The reaction mixture was poured into ice water, neutralized with acetic acid to pH=5 and stirred for 15 min. The resultant solid was filtered and washed with water. The crude material was crystallized from toluene. The yield was 50%.

NMR: (CDCl$_3$) δ 3.3 (t, 2H, CH$_2$), 3.5 (t, 2H, CH$_2$NH), 6.8 (d, 1H, 6'-H), 7.2 (m, 2H, 5-H, 6-H), 7.4 (d, 1H, 7-H), 7.6 (d, 1H, 4-H), 8.0 (d, 1H, 5'-H), 8.4 (bs, 1H, NH), 8.6 (s, 1H, NH), 8.8 (s, 1H, 3'-H).

EXAMPLE 11

N-(2-Carboxy-4-nitrophenyl)-tryptamine

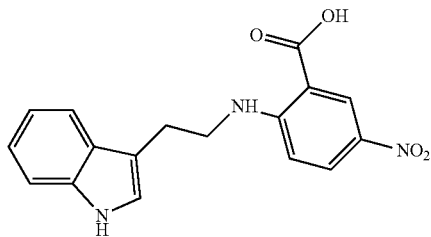

Procedure:

In a 250 ml round bottom flask DMF (10 eq.), tryptamine (1 eq.), 2-carboxy-4-nitrofluorobenzene (1 eq.) were added and stirred for 10 min. Then potassium carbonate (2.5 eq.) was added at room temperature. The stirring was continued for 2 hrs. TLC was monitored. The reaction mixture was poured into ice water, neutralized with acetic acid to pH=5 and stirred for 15 min. The resultant solid was filtered and washed with water. The crude material was crystallized from toluene. The yield was 50%.

NMR: (CDCl$_3$) δ 3.1 (t, 2H, CH$_2$), 3.6 (t, 2H, CH$_2$NH), 6.7 (d, 1H, 5'-H), 7.0 (m, 3H, 2-H, 5-H, 6-H), 7.4 (d, 1H, 7-H), 7.5 (d, 1H, 4-H), 8.1 (d, 1H, 4'-H), 8.8 (d, 1H, 3'-H), 8.9 (bs, 1H, NH), 10.4 (s, 1H, NH).

EXAMPLE 12

N-(2-Nitrophenyl)-5-methoxytryptamine

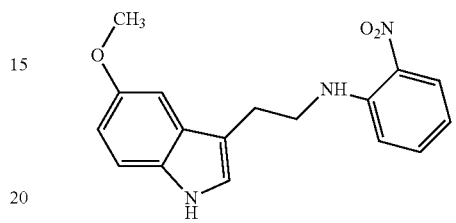

Procedure:

In a 250 ml round bottom flask DMF (10 eq.), 5-methoxytryptamine (1 eq.) and 2-nitrofluorobenzene (1 eq.) were added and stirred for 10 min. Then potassium carbonate (1.1 eq.) was added at room temperature. The stirring was continued for 2 hrs. TLC was monitored. The reaction mixture was poured into ice water and stirred for 15 min. The resultant solid was filtered and washed with water. The crude material was crystallized from methanol. The yield was 60%.

NMR: (CDCl$_3$) δ 3.2 (t, 2H, CH$_2$), 3.6 (t, 2H, CH$_2$NH), 3.8 (s, 3H, OCH$_3$), 6.6 (t, 1H, 4'-H), 6.8 (d, 2H, 6-H, 7-H), 7.0 (d, 1H, 4-H), 7.1 (s, 1H, 2-H), 7.3 (d, 1H, 6'-H), 7.9 (bs, 1H, NH), 8.2 (m, 2H, 3'-H, NH).

EXAMPLE 13

N-(4-Carboxy-2-nitrophenyl)-5-methoxytryptamine

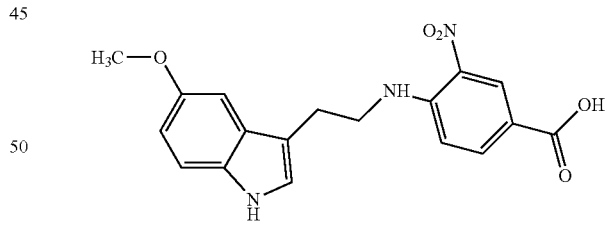

Procedure:

In a 250 ml round bottom flask DMF (10 eq.), 5-methoxytryptamine (1 eq.) and 4-carboxy-2-nitrofluorobenzene (1 eq.) were added and stirred for 10 min. Then potassium carbonate (2.5 eq.) was added at room temperature. The stirring was continued for 2 hrs. TLC was monitored. The reaction mixture was poured into ice water, neutralized with acetic acid to pH=5 and stirred for 15 min. The resultant solid was filtered and washed with water. The crude material was crystallized from toluene. The yield was 40%.

NMR: (CDCl$_3$) δ 3.5 (m, 4H, 2×CH$_2$), 3.8 (s, 3H, OCH$_2$), 6.7 (d, 1H, 6'-H), 6.9 (bs, 1H, 7-H), 6.95 (s, 1H, 2H), 7.1 (s, 1H, 4-H), 7.3 (d, 1H, 5'-H), 8.0 (bs, 1H, 6-H), 8.4 (bs, 1H, 3'-H), 8.8 (s, 1H, NH), 10.4 (s, 1H, NH).

EXAMPLE 14

N-(2-Carboxy-4-nitrophenyl)-5-methoxytryptamine

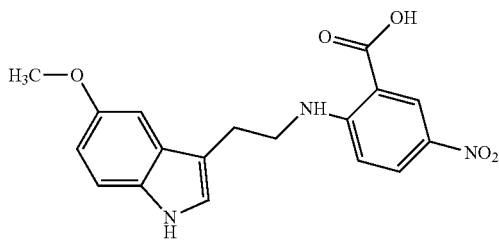

Procedure:

In a 250 ml round bottom flask DMF (10 eq.), 5-methoxytryptamine (1 eq.), 2-carboxy-4-nitrofluorobenzene (1 eq.) were added and stirred for 10 min. Then potassium carbonate (2.5 eq.) was added at room temperature. The stirring continued for 2 hrs. TLC was monitored. The reaction mixture was poured into ice water, neutralized with acetic acid to pH=5 and stirred for 15 min. The resultant solid was filtered and washed with water. The crude material was crystallized from toluene. The yield was 40%.

NMR: (CDCl$_3$) δ 3.1 (t, 2H, CH$_2$), 3.6 (t, 2H, NH), 3.8 (s, 3H, OCH$_3$), 6.6 (m, 2H, 4-H, 5'-H), 6.7 (m, 5H, Ar—H), 8.1 (d, 1H, 5-H), 8.7 (d, 1H, 3'-H), 8.9 (bs, 1H, NH), 10.5 (s, 1H, NH).

EXAMPLE 15

N-(2-cyano-4-nitrophenyl)-tryptamine

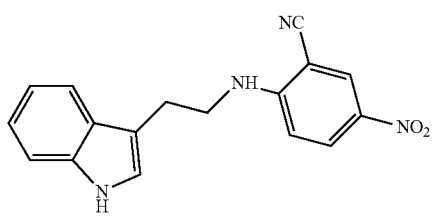

EXAMPLE 16

N-(2-nitro-4-bromophenyl)-tryptamine

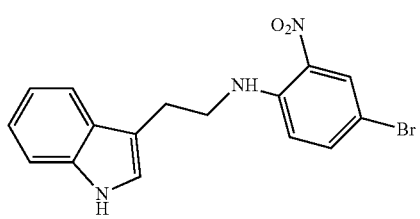

General procedure for the synthesis of N-(2-nitro-4-bromophenyl)-tryptamine and N-(2-cyano-4-nitrophenyl)-tryptamine 2×500 mg (2×1 equiv) of tryptamine were dissolved under an argon atmosphere in 2×2 ml of absolute ethanol in three different flasks of a Carousel parallel synthesizer. 4-bromo-1-fluoro-2-nitrobenzene (690 mg, 1 equiv) and 2-fluoro-5-nitrobenzonitrile (520 mg, 1 equiv) were added, respectively, in one of the two parallel flasks (A and B) and the obtained mixtures were allowed to react at room temperature under magnetic stirring. The course of the reactions was followed by TLC (dichloromethane as the eluent). Reactions A and B were completed after 8 and 2 hours, respectively. The two mixtures were then diluted with ca. 15 ml of diethyl ether and the resulting precipitates were collected by filtration and washed with additional Et$_2$O. TLC analyses showed in all precipitates residual traces of starting materials, thus each reaction mixture was purified by column chromatography on silica gel (approx. 20 grams). A mixture of petroleum ether/dichloromethane (8:2) was used until the starting nitroaromatic derivatives were eluted; subsequently, the target products were eluted by using dichloromethane. N-(2-nitro-4-bromophenyl)-tryptamine was collected as a red solid in 55% yield and finally N-(2-cyano-4-nitrophenyl)-tryptamine was obtained as a yellow solid in 40% yield.

NMR spectra of compounds, N-(2-nitro-4-bromophenyl)-tryptamine and N-(2-cyano-4-nitrophenyl)-tryptamine N-(2-nitro-4-bromophenyl)-tryptamine $^1$H NMR (DMSO-d$_5$, 400 MHz) δ 3.07 (t, 2H, J=6.9 Hz, CH$_2$), 3.62-3.68 (m, 2H, CH$_2$—NH), 6.98 (t, J=6.9 Hz, 1H, aromatic H), 7.06-7.10 (m, 2H, aromatic H), 7.26 (br s, 1H, aromatic H), 7.35 (d, J=8.0 Hz, 1H, aromatic H), 7.58 (d, J=8.3 Hz, 1H, aromatic H), 7.62 (dd, J$_1$=2.2 Hz, J$_2$=8.8 Hz, 1H, aromatic H), 8.13 (d, J=2.2 Hz, 1H, aromatic H), 8.20 (br t, J=5.4 Hz, 1H, CH$_2$—NH), 10.87 (br s, 1H, NH).

N-(2-cyano-4-nitrophenyl)-tryptamine $^1$H NMR (DMSO-d$_6$, 400 MHz) δ 3.01 (t, 2H, J=7.2 Hz, CH$_2$), 3.59-3.64 (m, 2H, CH$_2$—NH), 6.93 (d, J=9.6 Hz, 1H, aromatic H), 6.99 (t, J=7.4 Hz, 1H, aromatic H), 7.08 (t, J=6.9 Hz, 1H, aromatic H), 7.21 (br s, 1H, aromatic H), 7.34 (d, J=8.0 Hz, 1H, aromatic H), 7.55-7.60 (m, 2H, aromatic H+CH$_2$—NH), 8.15 (dd, J$_1$=2.1 Hz, J$_2$=9.5 Hz, 1H, aromatic H), 8.39 (d, J=2.1 Hz, 1H, aromatic H), 10.85 (br s, 1H, NH).

EXAMPLE 17

N-(3,4-dicyanophenyl)-tryptamine

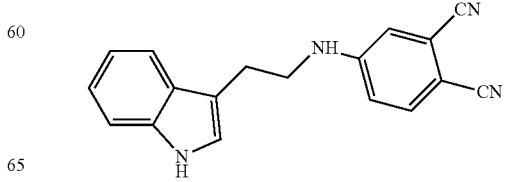

General procedure for the synthesis of N-(3,4-dicyanophenyl)-tryptamine

Under an argon atmosphere, a 100 ml three-necked round-bottom flask was charged with tryptamine (1.10 g, 1 equiv.) dissolved in EtOH (12 ml). To the solution 4-fluoro-phtahalonitrile (1.00 g, 1 equiv.) was then added in one portion. The resulting mixture was allowed to react under magnetic stirring for 25 h at room temperature. The reaction course was followed by TLC and HPLC-MS. The solvent was then removed by rotary evaporation and the crude product was chromatographed over a silica gel column by eluting with dichloromethane. The product was recovered as an off-white solid (880 mg, yield 35%).

$^1$H NMR (CDCl$_3$, 400 MHz) δ 3.13 (t, J=6.3 Hz, 2H, CH$_2$CH$_2$NH), 3.51-3.56 (m, 2H, CH$_2$CH$_2$NH), 4.54 (br t, J=5.3 Hz, 1H, CH$_2$CH$_2$NH), 6.69 (dd, J$_1$=2.3 Hz, J$_2$=8.6 Hz, 1H, aromatic H), 6.79 (d, J=2.5 Hz, 1H, aromatic H), 7.06 (d, J=2.3 Hz, 1H, aromatic H), 7.14-7.18 (m, 1H, aromatic H), 7.23-7.27 (m, 1H, aromatic H), 7.41 (br d, J=8.1 Hz, 1H, aromatic H), 7.46 (d, J=8.8 Hz, 1H, aromatic H), 7.57 (br d, J=8.1 Hz, 1H, aromatic H), 8.08 (br s, 1H, NH).

EXAMPLE 18

N-(3,4-dicyanophenyl)-5-methoxytryptamine

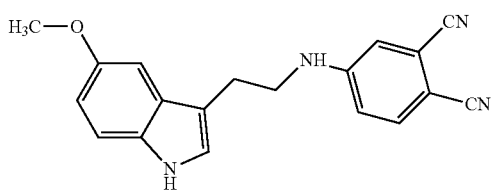

General procedure for the synthesis of N-(3,4-dicyanophenyl)-5-methoxytryptamine Under an argon atmosphere, a 100 ml three-necked round bottom flask was charged with 5-methoxytryptamine (1.33 g, 1 equiv.) dissolved in hot EtOH (20 ml). The solution was then cooled to room temperature and 4-fluoro-phtahalonitrile (1.00 g, 1 equiv.), was added in one portion. The resulting mixture was allowed to react under magnetic stirring for 20 h at room temperature. The reaction course was followed by TLC and HPLC-MS. The solvent was then removed by rotary evaporation and the crude product was chromatographed over a silica gel column by eluting with dichloromethane. The product was recovered as a white solid (490 mg, yield 22%).

$^1$H NMR (CDCl$_3$, 400 MHz) δ 3.09 (t, J=6.6 Hz, 2H, CH$_2$CH$_2$NH), 3.50-3.54 (m, 2H, CH$_2$CH$_2$NH), 3.85 (s, 3H, OCH$_3$), 4.55 (br t, J=5.1 Hz, 1H, CH$_2$CH$_2$NH), 6.69 (dd, J$_1$=2.3 Hz, J$_2$=8.8 Hz, 1H, aromatic H), 6.80 (d, J=2.8 Hz, 1H, aromatic H), 6.90 (dd, J$_1$=2.0 Hz, J$_2$=8.8 Hz, 1H, aromatic H), 6.98 (d, J=2.9 Hz, 1H, aromatic H), 7.03 (d, J=2.3 Hz, 1H, aromatic H), 7.30 (d, J=8.8 Hz, 1H, aromatic H), 7.47 (d, J=8.8 Hz, 1H, aromatic H), 7.97 (br s, 1H, NH).

EXAMPLE 19

2-(2-aminobenzoyl)-N-2-nitrophenylethylamine

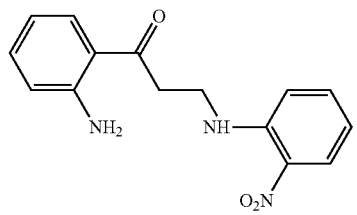

2 ml of 2-nitro-fluorobenzene were reacted in 20 ml DMF, at room temperature, with 5 g of kynuramine and 3 g of potassium carbonate, to yield the desired product; reaction time was 2 h. The reaction mixture was placed in 250 ml of water and stirred. It was extracted into ethylacetate (2×100 ml), ethylacetate layer was washed twice with water (50 ml), dried with sodium sulphate and the solvent was distilled off. The crude material was purified by column chromatography run with ethylacetate and hexane mixture (1:9).

Yield referred was 500 mg.

$^1$H NMR (DMSO-d$_6$, 500 MHz) δ 3.35 (t, 2H, NHCH$_2$CH$_2$, J=6.6 Hz), 3.69 (q, 2H, NHCH$_2$CH$_2$, J=6.4 Hz), 6.52 (t, 1H, aromatic, J=7.6 Hz), 6.68 (t, 1H, aromatic, J=7.8 Hz), 6.75 (d, 1H, aromatic, J=8.3 Hz), 7.13 (d, 1H, aromatic, J=8.7 Hz), 7.23 (m, 3H, 1 aromatic H+NH$_2$), 7.55 (t, 1H, aromatic, J=7.8 Hz), 7.77 (d, 1H, aromatic, J=8.1 Hz), 8.06 (d, 1H, aromatic, J=8.7 Hz), 8.23 (t, 1H, NHCH$_2$CH$_2$, J=5.6 Hz)

BIOLOGICAL TESTING OF COMPOUNDS OF THE INVENTION

Experiment 1

Evaluation of GSK3β Activity

Compounds were evaluated for inhibition against purified GSK3β. GSK3β was expressed in and purified from insect Sf9 cells. Compounds (10 µM) were assayed; following a 1/100 dilution of the enzyme in 1 mg/ml BSA, 10 mM DTT, with 5 µl of 40 µM GS-2 peptide as a substrate, in a buffer, in the presence of 15 µM [γ-$^{32}$P]ATP (3000 Ci/mmol; 1 mCi/ml) in a final volume of 30 µl. After 30-min incubation at 30° C., 25-µl aliquots of supernatant were spotted onto 2.5×3 cm pieces of Whatman P81 phosphocellulose paper, and, 20 s later, the filters were washed five times (for at least 5 min each time) in a solution of 10 ml of phosphoric acid/liter of water. The wet filters were counted in the presence of 1 ml of scintillation fluid. Table 1 presents the GSK3S activity inhibition by compounds of the present patent application.

TABLE 1

| Tested Substance | GSK3β Activity Inhibition IC50 |
|---|---|
| N-(2-Nitrophenyl)-tryptamine | 9.9 µM |
| N-(2-cyano-4-nitrophenyl)-tryptamine | 12.7 µM |
| N-(2-Nitrophenyl)-5-methoxytryptamine | 14.1 µM |
| N-(2-Carboxy-4-nitrophenyl)-tryptamine | 14.2 µM |
| N-(3,4-dicyanophenyl)-tryptamine | 14.8 µM |
| N-(3,4-dicyanophenyl)-5-methoxytryptamine | 16.8 µM |

TABLE 1-continued

| Tested Substance | GSK3β Activity Inhibition IC50 |
|---|---|
| 2-(2-aminobenzoyl)-N-2-nitrophenylethylamine | 18.5 μM |
| N-(4-Carboxy-2-nitrophenyl)-5-methoxytryptamine | 21.7 μM |
| 2-(2-aminobenzoyl)-N-2-nitro-4-cyano-phenylethylamine | 29.3 μM |

This experiment revealed that N-(2-Nitrophenyl)-tryptamine, N-(2-cyano-4-nitrophenyl)-tryptamine, N-(2-nitrophenyl)-5-methoxytryptamine, N-(2-carboxy-4-nitrophenyl)-tryptamine, N-(3,4-dicyanophenyl)-tryptamine, N-(3,4-dicyanophenyl)-5-methoxytryptamine, N-(4-carboxy-2-nitrophenyl)-5-methoxytryptamine and 2-(2-aminobenzoyl)-N-2-nitro-4-cyano-phenylethylamine have a significant inhibiting activity on GSK3β activity.

Experiment 2

Evaluation of Anti-Parkinsonian Activity Using MPTP-Treated Mice with/without a Sub Threshold Dose of L-DOPA Animals: six month old male C57 BL/6 mice, weighing 22-25 g were used. Following arrival at the laboratory, the mice were allowed to acclimatize for two weeks in a room with controlled temperature (21±1° C.), and a constant light-dark schedule (12 hr on/12 hr off, lights on between 06.00 and 18.00 hrs). Free access to food and water was maintained throughout. They were housed in groups of 12 animals and tested only during the hours of light (08.00-15.00 hrs). All testing was performed in a normally lighted room. Each test chamber (i.e. activity test cage) was placed in a soundproofed wooden box with 12 cm thick walls and front panels and had a dimmed lighting.

Behavioural measurements and apparatus: An automated device, consisting of macrolon rodent test cages (40×25×15 cm), each placed within two series of infra-red beams (at two different heights, one low and one high, 2 and 8 cm, respectively, above the surface of the sawdust, 1 cm deep), was used to measure spontaneous and/or drug-induced motor activity of 1-methyl 4-phenyl 1,2,3,6-tetrahydropyridine (MPTP) and control mice. The following parameters were measured: LOCOMOTION was measured by the low grid of infrared beams. Counts were registered only when the mouse in the horizontal plane, ambulating around the test-cage. REARING was registered throughout the time when at least one high level beam was interrupted, i.e. the number of counts registered was proportional to the amount of time spent rearing. TOTAL ACTIVITY was measured by a sensor (a pick-up similar to a gramophone needle, mounted on a lever with a counterweight) with which the test cage was constantly in contact. The sensor registered all types of vibration received from the test cage, such as those produced both by locomotion and rearing as well as shaking, tremors, scratching and grooming.

Behavioral measurements (locomotion, rearing and total activity): Twelve days after MPTP injections (2×40 mg/kg, s.c., 24 hr interval), the mice were administered orally with the different compounds at 3 mg/kg or vehicle (0.1% Tween-80 in 1% methylcellulose) and immediately thereafter placed in the activity test chambers and their motor behaviors were monitored for 60 min. After 60 min, the mice were injected with 5 mg/kg L-Dopa (s.c) and then replaced in the test chamber and activity measurements maintained for an additional 300 min.

Table 2 presents the locomotion, rearing and total activity counts of MPTP-treated and control mice administered either tested substances or vehicle administered with a sub threshold dose of L-Dopa.

TABLE 2

| TREATMENT | LOCOMOTION | REARING | TOTAL ACTIVITY |
|---|---|---|---|
| Vehicle | 100% | 100% | 100% |
| MPTP + vehicle | 16% | 25% | 46% |
| MPTP + N-(4-bromo-2-nitrophenyl)-5-methoxytryptamine | 16% | 24% | 46% |
| MPTP + 2-(2-aminobenzoyl)-N-2-nitrophenylethylamine | 17.6% | 25% | 45% |
| MPTP + N-(2-carboxy-4-nitrophenyl)-tryptamine | 16% | 25% | 45% |
| MPTP + N-(3,4-dicyanophenyl)-tryptamine | 18% | 25% | 47% |
| MPTP + N-(3,4-dicyanophenyl)-5-methoxytryptamine | 19% | 27% | 48% |
| MPTP + 2-(2-aminobenzoyl)-N-2-nitro-4-cyano-phenylethylamine | 17% | 29% | 46% |
| MPTP + N-(4-Carboxy-2-nitrophenyl)-5-methoxytryptamine | 22% | 30% | 46% |
| MPTP + N-(4-methylsulfonyl-2-nitropheny)-5-methoxytryptamine | 41% | 74% | 70% |
| MPTP + N-(2-nitrophenyl)-5-methoxytryptamine | 44% | 90% | 73% |
| MPTP + N-(2-cyano-4-nitrophenyl)-tryptamine | 52% | 98% | 73% |
| MPTP + 2-(2-aminobenzoyl)-N-2-nitro-4-methylsulfonyl-phenylethylamine | 54% | 100% | 72% |
| MPTP + N-(2-Nitrophenyl)-tryptamine | 53% | 100% | 90% |

2(2-aminobenzoyl)-N-2-nitro-4-methylsulfonyl-phenylethylamine, N-(4-methylsulfonyl-2-nitrophenyl)-5-methoxytryptamine, N-(2-nitrophenyl)-5-methoxytryptamine, N-(2-nitrophenyl)-tryptamine and N-(2-cyano-4-nitrophenyl)-tryptamine (3 mg/kg) significantly reversed the motor deficits of MPTP-treated mice when combined with a sub-threshold (inactive) dose of L-Dopa.

Experiment 3

Electrophysiological Characterisation of NMDA-Activated Currents in Freshly Isolated Hippocampal Neurones of Rat Isolation of hippocampal neurons: Wistar rats (12-14 days) were decapitated without anesthesia and the hippocampus was removed. It was manually cut into slices (0.2-0.4 mm), in a solution containing (mM): 150 NaCl; 5 KCL; 1.25 $NaH_2PO_4$; 2 $CaCl_2$; 2 $MgCl_2$; 26 $NaHCO_3$; 20 glucose. Slices were preincubated in this solution for 30 min at room temperature. The enzymatic treatment proceeded in the same solution with lower $Ca^{2+}$ concentration (0.5 mm) containing 0.4 mg/ml protease from *aspergillus oryzae*. The incubation in the enzyme solution proceeded at 32° C. within 10 min. Slices were kept subsequently in enzyme-free solution containing normal $Ca^{2+}$±concentration and used within 6-8 h for obtaining isolated neurons. Throughout the entire procedure the solutions were continuously saturated with a 95% $O_2$ and 5% $CO_2$ gas mixture to maintain pH of 7.4. For cell dissociation the slice was transferred into the extracellular solution containing (mM): 150 NaCl; 5 KCl; 2 $CaCl_2$; 10 n-2-hydroxyethylpiperazine-n'-2-ethanesulphonic acid (Hepes); pH adjusted with NaOH to 7.4. Single cells were isolated from CA and CA3 zones of hippocampal slices by vibrodissociation method. They had a diameter 10-15 µm and preserved a small part of dendritic tree. After isolation they were usually suitable for the recording for 1-2 h.

Salines and chemicals: The contents of the extracellular solution was as follows (in mM): 130 NaCl, 5KCl, $2CaCl_2$, 20 n-2-hydroxyethylpiperazine-n'-2-ethansulfonic acid (Hepes); 0.1 µm TTX, 10 µm glycine, 300 mm 1-aspartate; pH was adjusted with NaOH to 7.4.

The contents of the intracellular solution were as follows (in mM): 110 CsF, 20 Tris-HCl (pH=7.2). L-aspartate and glycine solutions were prepared on the day of experiment. The tested substances were dissolved in DMSO.

Current recording and data analysis: The drug-containing solutions were applied by the fast "concentration clamp" method using "jumping table" set-up. The currents were recorded with patch clamp technique in the whole-cell configuration. Recording of the currents was performed using EPC-7 L/M patch-clamp amplifier.

NMDA-activated currents: The currents were filtered at 3 kHz (three-pole active Bessel filter) digitally sampled at the rate 6000 µs per point for NMDA activated currents. NMDA-induced transmembrane currents were measured in the presence of 10 µM glycine and 300 µM L-aspartate in the control and test solutions. The currents were recorded at holding potential –70 mV.

Calculations: The inhibition of current at 1 µM of the substance was averaged at least for 4 cells. The effect of substance was measured as the mean ratio I/Io where I was the current under the action of substance and Io was the current in control conditions.

The action of 1 µM tested substances on NMDA-activated currents are shown in Table 3.

TABLE 3

| Tested Substance | % Inhibition | |
|---|---|---|
| (1 µM) | Peak Current | Steady State Current |
| N-(3,4-dicyanophenyl)-tryptamine | 93.4% | 66.4% |
| N-(2-Nitrophenyl)-tryptamine | 90.93% | 66.83% |
| N-(2-Carboxy-4-nitrophenyl)-tryptamine | 76.7% | 70.4% |
| N-(4-Carboxy-2-nitrophenyl)-5-methoxytryptamine | 89.92% | 74.14% |
| N-(2-Nitrophenyl)-5-methoxytryptamine | 78% | 77.3% |
| N-(4-bromo-2-nitrophenyl)-5-methoxytryptamine | 104.2% | 78.18% |
| N-(3,4-dicyanophenyl)-5-methoxytryptamine | 84.4% | 78.4% |
| N-(2-cyano-4-nitrophenyl)-tryptamine | 83.1% | 82.44% |
| N-(2-nitro-4-bromophenyl)-tryptamine | 95.8% | 83% |
| N-(2-bromo-4-nitrophenyl)-5-methoxytryptamine | 91.53% | 86.57% |
| 2-(2-aminobenzoyl)-N-2-nitro-4-cyano-phenylethylamine | 85.95% | 87.24% |

TABLE 3-continued

| Tested Substance | % Inhibition | |
|---|---|---|
| (1 µM) | Peak Current | Steady State Current |
| N-(2-cyano-4-nitrophenyl)-5-methoxytryptamine | 96.21% | 88.21% |
| 2-(2-aminobenzoyl)-N-2-nitro-4-bromo-phenylethylamine | 90.85% | 88.77% |
| 2-(2-aminobenzoyl)-N-2-bromo-4-nitro-phenylethylamine | 86.23% | 90.78% |
| N-(4-Carboxy-2-nitrophenyl)-tryptamine | 101.6% | 92.84% |
| N-(2-Carboxy-4-nitrophenyl)-5-methoxytryptamine | 84% | 93.6% |

This experiment revealed that N-(3,4-dicyanophenyl)-tryptamine, N-(2-nitrophenyl)-tryptamine, N-(2-carboxy-4-nitrophenyl)-tryptamine, N-(4-carboxy-2-nitrophenyl)-5-methoxytryptamine, N-(2-nitrophenyl)-5-methoxytry ptamine, N-(4-bromo-2-nitrophenyl)-5-methoxytryptamine, N-(3,4-dicyanophenyl)-5-methoxytryptamine, N-(2-cyano-4-nitrophenyl)-tryptamine and N-(2-nitro-4-bromophenyl)-tryptamine have a significant blocking activity on NMDA-activated currents.

The invention claimed is:

1. A method for treating a disease, disorder or condition selected from the group consisting of Parkinson's disease, Huntington's disease, Amyotrophic Lateral Sclerosis, multiple sclerosis, Alzheimer's disease, diabetes, schizophrenia, or depression, which method comprises administering to an animal or human in need of such treatment an effective amount of a compound of the formula:

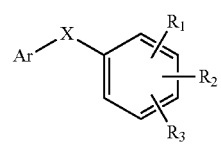

wherein

R1 is alkylsulfonyl;

each of R2 and R3 is independently selected from hydrogen, carboxy, nitro, alkylsulfonyl, aminosulfonyl, alkyl aminosulfonyl, halogen, cyano, C1-4 alkyl, C1-4 alkoxy, NR'R", aryl, aryl-C1-4 alkyl, or aryl-C1-4 alkoxy, and each of R' and R" is independently H or C1-4 alkyl, or R'=R"=C1CH2CH2, or NR'R" constitutes a saturated heterocyclic ring containing 3-8 ring members;

X is:

—(CH2)n-Y— wherein Y is: >NH; n is 0-4; and any carbon of the —(CH2) n- may be substituted by 1-2 substituents independently selected from halogen, carboxy, C1-4 alkyl, C1-4 alkoxy, OH, NH2 or acyl; and Ar is a kynurenine/kynuramine metabolite of a 3-indole:

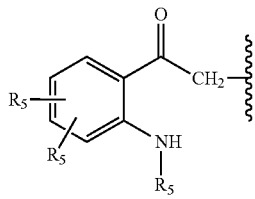

wherein each R5 independently is hydrogen, halogen, C1-4 alkyl, C1-4 alkoxy, OH, NR'R" as defined above, nitro, aryl, aryl-C1-4 alkyl, or aryl-C1-4 alkoxy;

or a pharmaceutically acceptable salt thereof.

2. A method for treating a disease, disorder or condition selected from the group consisting of Parkinson's disease, Huntington's disease, Amyotrophic Lateral Sclerosis, multiple sclerosis, Alzheimer's disease, diabetes, schizophrenia, or depression, which method comprises administering to an animal or human in need of such treatment an effective amount of the compound 2-(2-aminobenzoyl)-N-2-nitro-4-methylsulfonyl-phenylethylamine or a pharmaceutically acceptable salt thereof.

3. The method of claim 1, wherein the disease, disorder or condition is Parkinson's disease, Huntington's disease, Amyotrophic Lateral Sclerosis, multiple sclerosis, or Alzheimer's disease.

4. The method of claim 3, wherein the disease, disorder or condition is Parkinson's disease.

5. The method of claim 2, wherein the disease, disorder or condition is Parkinson's disease, Huntington's disease, Amyotrophic Lateral Sclerosis, multiple sclerosis, or Alzheimer's disease.

6. The method of claim 5, wherein the disease, disorder or condition is Parkinson's disease.

7. The method of claim 1, wherein the disease, disorder or condition is diabetes.

8. The method of claim 1, wherein the disease, disorder or condition is schizophrenia.

9. The method of claim 1, wherein the disease, disorder or condition is depression.

* * * * *